(12) United States Patent
Selby et al.

(10) Patent No.: US 11,273,099 B2
(45) Date of Patent: Mar. 15, 2022

(54) DOSE CONTAINER (75) Inventors: Robert Gordon Maurice Selby, Royston (GB); Neil Pollock, Royston (GB); Daniel Crichton, Cambridge (GB); Douglas Robert Saunders Bradshaw, Melbourn (GB)

(73) Assignee: THE TECHNOLOGY PARTNERSHIP, PLC., Royston (GB)

( * ) Notice: Subject to any disclaimer, the term of this patent is extended or adjusted under 35 U.S.C. 154(b) by 1899 days.

(21) Appl. No.: 14/117,800

(22) PCT Filed: May 16, 2012

(86) PCT No.: PCT/GB2012/051082
§ 371 (c)(1),
(2), (4) Date: Apr. 4, 2014

(87) PCT Pub. No.: WO2012/156725
PCT Pub. Date: Nov. 22, 2012

(65) Prior Publication Data
US 2014/0217197 A1   Aug. 7, 2014

(30) Foreign Application Priority Data

May 16, 2011  (GB) ...................................... 1108102
Mar. 14, 2012  (GB) ...................................... 1204429

(51) Int. Cl.
*A61J 1/14* (2006.01)
*A61M 15/00* (2006.01)
(Continued)

(52) U.S. Cl.
CPC . *A61J 1/14* (2013.01); *A61J 3/07* (2013.01); *A61M 15/0028* (2013.01);
(Continued)

(58) Field of Classification Search
CPC ............ B65D 81/3211; B65D 81/3222; B65D 51/2835; B65D 51/2857; B65D 51/224;
(Continued)

(56) References Cited

U.S. PATENT DOCUMENTS 1,247,088 A   11/1917  Vilbiss
1,839,193 A   1/1932  Blanchard
(Continued)

FOREIGN PATENT DOCUMENTS

CN   101795723   8/2010
EP   0615470   12/1995
(Continued)

*Primary Examiner* — Anthony D Stashick
*Assistant Examiner* — Blaine G Neway
(74) *Attorney, Agent, or Firm* — Tarolli, Sundheim, Covell & Tummino LLP (57) ABSTRACT

A unit dose container for holding a single dose of a given liquid, the container comprising: a chamber (8) in which, in use, the given liquid is stored, the chamber having a wall through which, in use, the liquid is to be supplied; a release mechanism (7), at least part of which is internal to, or forms part of the wall of the chamber, the release mechanism being movable relative to the chamber between first and second positions; and means for allowing the release mechanism (7) to move from the first to the second positions, thereby opening a passage through the wall so that the liquid can exit the chamber (8), the means including at least one flexible wall portion.

18 Claims, 8 Drawing Sheets

(51) Int. Cl.
  *A61J 3/07* (2006.01)
  *B05B 17/00* (2006.01)
  *A61M 11/06* (2006.01)
  *B65D 25/08* (2006.01)
  *A61M 11/00* (2006.01)

(52) U.S. Cl.
  CPC .... *A61M 15/0035* (2014.02); *A61M 15/0041* (2014.02); *A61M 15/0053* (2014.02); *A61M 15/0063* (2014.02); *A61M 11/005* (2013.01); *A61M 11/06* (2013.01); *A61M 15/0085* (2013.01); *A61M 2202/04* (2013.01); *B05B 17/0638* (2013.01); *B65D 25/08* (2013.01)

(58) Field of Classification Search
  CPC ....... B65D 51/2814; B65D 2575/3254; A61M 15/0035; A61M 15/0041; A61J 1/14
  See application file for complete search history.

(56) References Cited

U.S. PATENT DOCUMENTS

| | | | | |
|---|---|---|---|---|
| 3,583,602 A * | 6/1971 | Gruber | ..................... | B65D 1/32 222/92 |
| 3,738,540 A * | 6/1973 | Morane | ................... | B65D 83/38 222/397 |
| 3,951,622 A * | 4/1976 | Wilk | ....................... | A01N 25/18 206/439 |
| 4,103,772 A * | 8/1978 | Wiegner | ............ | B65D 81/3222 206/222 |
| 4,157,787 A * | 6/1979 | Schwartz | .................. | A61L 9/12 239/56 |
| 4,247,001 A * | 1/1981 | Wiegner | ............ | B65D 81/3222 206/222 |
| 4,950,237 A * | 8/1990 | Henault | ............. | B65D 81/3211 222/129 |
| 6,443,307 B1 | 9/2002 | Burridge | | |
| 6,561,232 B1 * | 5/2003 | Frutin | ................ | B65D 51/2857 141/100 |
| 6,910,573 B2 * | 6/2005 | Deans | ............... | B65D 81/3211 206/222 |
| 7,252,091 B1 * | 8/2007 | Wayne | ................... | A45D 19/02 132/112 |
| 7,621,403 B2 * | 11/2009 | Althoff | .................. | A45D 40/24 206/443 |
| 8,308,388 B2 * | 11/2012 | Guay | .................... | A45D 34/04 401/198 |
| 2006/0183216 A1 | 8/2006 | Handique et al. | | |
| 2008/0283439 A1 | 11/2008 | Sullivan et al. | | |
| 2011/0174642 A1 * | 7/2011 | Coon | ................ | B65D 51/2835 206/222 |

FOREIGN PATENT DOCUMENTS

| | | |
|---|---|---|
| EP | 0696234 | 11/1999 |
| EP | 12106196 | 6/2001 |
| WO | 2005102058 | 11/2005 |
| WO | 2009009013 | 1/2009 |

* cited by examiner

DOSE CONTAINER

FIELD OF THE INVENTION

This invention relates to liquid dispensing devices including, but not limited to droplet generating devices such as electronic spray devices in which a vibrating perforate membrane is used to generate liquid droplets. In particular, it relates to how pre-metered unit dose capsules can be used to maintain sterility and define a dose volume.

BACKGROUND OF THE INVENTION

Introduction & Prior Art on Dose Containers

In the medical field the ability to dispense multiple metered doses while maintaining sterility of the stored liquid without the need for preservatives is highly prized. This both allows accurately metered doses to be created at the filling stage rather than by in-device metering and greater freedom for formulations by removing the need for preservatives. In the consumer field applications of fragrance and air freshener benefit from seal dose containers through reasons of convenient handling, and the elimination of spillage and/or cross contamination.

Electronic atomisers that use ultrasonic vibration to generate liquid droplets are well known in the art and have found use in a wide range of fields including medical drug delivery and the treatment of air (for example fragrance delivery and humidification).

Devices such as jet nebulisers and thermal fragrance dispensers can also benefit from this method with the respective advantages of dose metering and sterility and avoidance of spillage and cross contamination when for example changing fragrances.

Product Form Discussion

Size requirements for portable devices place an emphasis on efficient packaging to yield a compact form. Cost requirements drive the need to minimise both the total number of components and in particular the number of components that are disposable.

For a range of devices it is desirable to make use of a master-cartridge model in which a master unit can be used to deliver liquid contained in a cartridge in which the cartridge can be replaced. All liquid contacting components ideally reside on the cartridge and as many non-liquid contacting components as possible reside on the master. This minimises the cost of the cartridge whilst avoiding cross-contamination between cartridges. Examples of fields where such an approach finds use include the medical field and the consumer fragrance field. In the medical field dose sterility can be critical and this can be achieved by containing each dose in its own cartridge (or capsule). Also in the medical field the same master device may be designed to be used with more than one patient and cross-contamination must be avoided. In the fragrance field, each cartridge may contain a different fragrance and again cross-contamination must be avoided. Other fields in which similar demands are met will be obvious to someone skilled in the art.

SUMMARY OF THE INVENTION

Use of Unit Doses

In summary, there is a desire for a device to have one or more of the following characteristics:

Seal metered fluid dose for storage
Ability to release dose in preparation for delivery
Preparation for dose delivery suitable for unskilled operator
Allow means for pressure control, for priming and operation
Convenient According to a first aspect of the invention, there is provided a sealed fluid container comprising; a means for retaining the fluid within the container and a means for releasing the dose when required. Additionally, there may be a facility to control the pressure applied to the measured dose once the dose has been released to the dispense mechanism. Positive pressure may be needed for priming, and negative or neutral pressure for fluid control. A particular application for this invention is for devices which use an ultrasonically vibrating perforate member such as that described in EP0615470, in which the vibrating perforate plate is vibrated in a bending mode to generate liquid droplets. A second application includes droplet delivery means such as jet nebulisers.

According to a second aspect of the invention, there is provided
Sealed dose unit, where the seal for the dose is provided by either:
a valve
a frangible membrane, or
where the seal for one dose is provided by the previous or subsequent dose by means of a stackable format.

In the case of the vibrating perforate membrane device, the application of negative pressure (a fraction of an atmosphere below ambient) applied to the fluid in contact with the perforate membrane can be beneficial for performance. In this case the design of the dose container can have certain features to allow the generation of the negative pressure by displacement of a flexible wall so as to increase the internal volume.

In the case of a jet nebuliser or capillary fed fragrance dispenser there may be a need to be able to first prime the fluid feed such that fluid is advanced to the dispense region and subsequently reduce the pressure such that the liquid is retained in the correct position by the favourable capillary forces that form part of the dispense mechanism against a slight negative pressure.

According to a third aspect of the invention, there is provided a unit dose container for holding a single dose of a given liquid, the container comprising: a chamber in which, in use, the given liquid is stored, the chamber having a wall through which, in use, the liquid is to be supplied; a release mechanism, at least part of which is internal to, or forms part of the wall of, the chamber, the release mechanism being movable relative to the chamber between first and second positions; and means for allowing the release mechanism to move from the first to the second positions, thereby opening a passage through the wall so that the liquid can exit the chamber, the means including at least one flexible wall portion.

Various modifications and preferred features are set out throughout the specification and, in particular, in the dependent claims. Any of those preferred features could be combined with any of the first to third aspects of the invention described above.

Application

The invention has application in pre-metered dose delivery generally, but specifically in medical applications— where sterility of doses is of paramount importance, or for fragrance delivery—where cross contamination and spillage is to be avoided.

The invention has specific applicability to Patent Application number GB1108102.3 in which an electronic spray device, using a vibrating perforate membrane to generate liquid droplets, has its functionality improved by a magnetic coupling, enabling the separation of the vibrating membrane from its driver element.

The invention is also applicable to Patent number EP0615470 (which describes a low-cost fluid droplet generating device for spraying fluids by means of a pzt-driven vibrating perforate membrane, comprising a composite thin-walled structure operating in a bending mode, and arranged to allow efficient operation without edge constraints); and to jet nebulisers known in the art such as U.S. Pat. Nos. 1,247,088A, 1,839,193A, 4,746,067A.

BRIEF DESCRIPTION OF THE DRAWINGS

Examples of the present invention will now be described with reference to the accompanying drawings, in which.

DETAILED DESCRIPTION OF THE INVENTION

Generally Applicable Unit Dose Design

The container preferable consists of a chamber capable of being sealed as a closed chamber to contain the fluid dose. This may consist of an open structure with provision for sealing with one or two foil or polymer foils, and or use of a valve arrangement.

The container preferable has a design compatible with being filled with a dose and then sealing the dose for storage. For example, there may be provision of a flat surface for sealing lidding foil of film following filling. Lidding with materials such as aluminium foils provided by companies such as Constantia, Tekni-Films. Or engineered polymer films such as Aclar provided by Honeywell, or 3M's Scotchpak PET films such as HB-P69733 which uses a ceramic oxide coating to provide a moisture and oxygen barrier The container preferable includes a mechanism to allow the release of the dose at the point of use. This mechanism should be compatible with operation either manually by means of a release button, lever or similar, built into the dispensing device or directly part of the unit dose. This mechanism is preferably actuated by an action external to the dose container itself, such as by a user pressing a part of the device or an operating button or lever, or for example when the invention is used in an inhaler type device, the actuation could be by a user inhaling.

Any part of the feature used to release the dose which is wetted by the dose, will preferably be used only once to minimise potential for contamination of the dose from both a sterility point of view and from minimising cross contamination of fragrances in the case of fragrance dispense. As such any wetted dose release components are preferably unique to the unit dose.

The container is preferably capable of convenient handling as a single dose by the user or automatically by an indexing mechanism within the delivery device, either as multiple individual doses or as part of a collated cartridge comprising a convenient number of doses, for example 30 doses for a month's daily use.

In view of the single use nature of the unit dose it is important to minimise the cost of manufacture of the units and as such minimising the number of components and simplifying the method of construction is key. By careful design moulded plastic components can provide more than one function and are economic to make in volume.

The container may be constructed from materials compatible with terminal sterilisation or aseptic filling and from materials capable of providing the required barrier properties to both vapour and gaseous transmission. Typically this protection can be provided by suitable material selection, including glass as the ultimate barrier material or suitable thicknesses of polymers such as LDPE, PP, or Nylon, or by engineered material with enhanced barrier properties such as ceramic oxide coatings.

The container is preferably designed such that the unit dose container is compatible with application to ultrasonically vibrating actuators such as a bending mode actuator, e.g. EP0615470 or a longitudinal actuator such as described in EP0696234.

Similarly if to be used with a jet nebuliser or similar capillary fed delivery device such as fragrance dispensers then the container will need features to allow effective and convenient sealing to the capillary structure, such as a tubular form allowing a radial compression seal to be formed.

Typical Operational Sequence

The typical operational steps are outlined by the followings steps:

Load unit dose into dispense position, either manually with suitable guidance features to aid location, or automatically by an indexing mechanism Couple the dose to the dispensing mechanism, e.g. magnetically couple to a bending mode ultrasonic actuator, or connect the fluid path by means of a radial seal between tubular features for a capillary dispense device such as a jet nebuliser, or simply locate the unit dose ready for dispense if the dispense features are incorporated into the unit dose.

Release the unit dose in preparation for delivery by one of the following; manually; as part of a priming step or subsequently as a breath triggered action for medical applications. This step may also include a fluid priming step to drive the fluid to the point of dispense and optionally a pressure reduction method to reduce the pressure to just below ambient.

Commence dispensing, again either manually, automatically as a timed dispense sequence or triggered in some way such as breath triggering or movement detection for drug delivery or fragrance delivery respectively.

Typically continue to deliver the dose until completion, either as continuously or in response to a triggering event.

Aspects of the Invention

Valved or foil separated unit does container designs according to the invention have the ability to meet any or all of these requirements. A range of embodiments of the invention are now disclosed with reference to the following figures.

Figure 8:
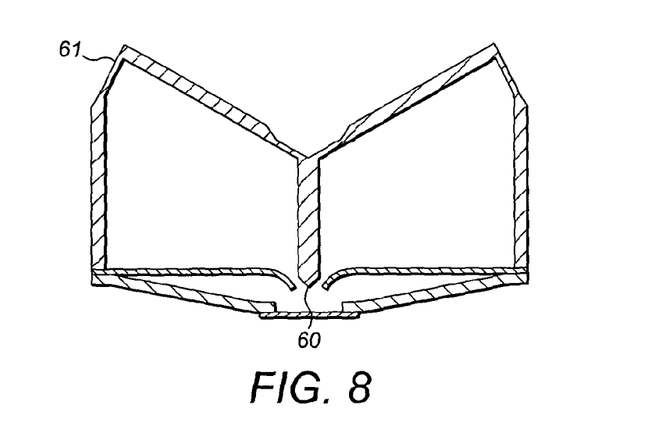
Figure 9:
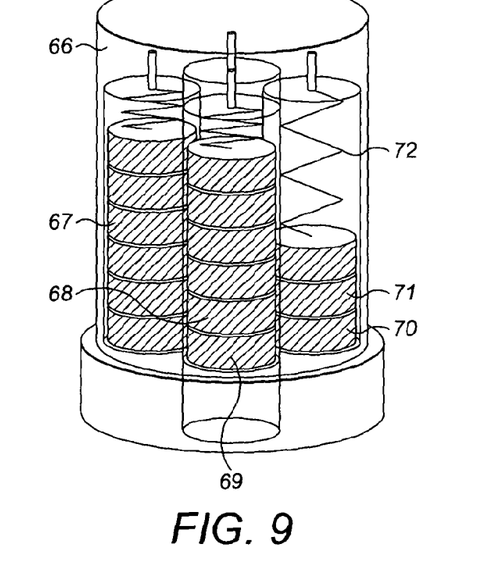
FIG. 9 shows a stacking device for holding container of the invention.

The forms of dose container shown in FIGS. 1 to 5 may be applicable to separable membrane devices as described in application number GB1108102.3, and equally to bonded membrane designs where the actuator would be permanently bonded to the perforate membrane EP0615470. With some adaption, obvious to those skilled in the art, these approaches can be applied more widely to devices such as jet nebuliser and other fluid dispensing apparatus and some example adaptations are shown in FIGS. 8 and 9

Figure 1:
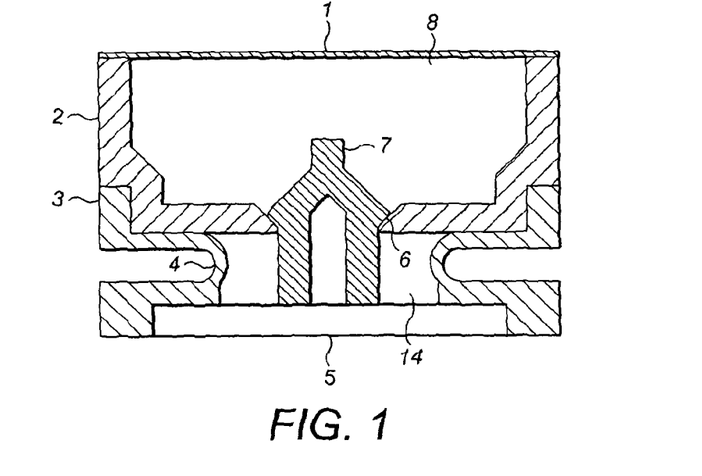
FIGS. 1 and 2 show one example of a container using a valve, in the closed and open positions respectively.
Figure 2:
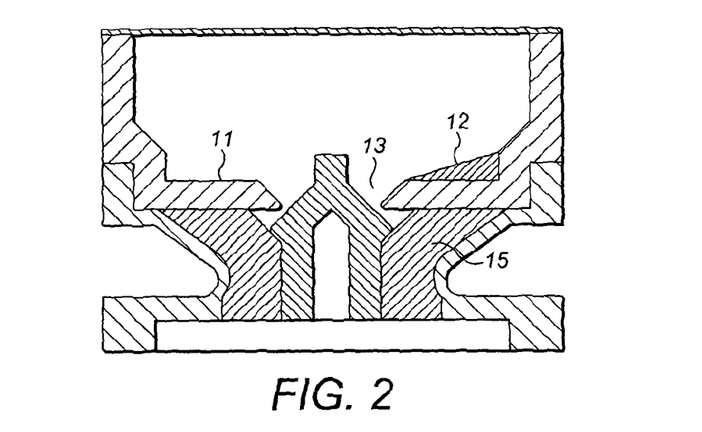

FIGS. 1 and 2 shows one implementation where an internal valve 7 retains a metered dose within the chamber 8 separated from the perforate membrane 5 during storage. The dose chamber is formed by the walls 2, valve 7, and foil seal 1 which is fitted after filling. The perforate membrane is held in a flexible housing 3, having a flexible wall portion 4. The flexible wall portion may, in any of the embodiments, additionally be resilient such that, after release of any actuation force, the flexible housing returns to its original configuration or something close to that configuration. It is preferable that the resilience allows the pressure inside the housing to be equalised with that outside the housing. Alternatively, the resilience may cause the housing to return to a position in which a negative pressure is generated within the chamber, i.e. a pressure lower than the ambient pressure. This negative pressure is likely to be caused, in the membrane embodiment(s), once the released fluid has coated the perforate membrane and the surface tension of the liquid on the membrane is sufficient to prevent the ingress of air as the flexible wall portion returns to its at rest position. However, other mechanisms that seal the chamber prior to the release of any or all of an actuating force, and therefore before the chamber has expanded to equalise the pressure, could be used, such as valves or the like. The dose is retained in the dose chamber by the valve 7 until the point of use. To release the dose the valve 7, is opened by movement of the flexible member 4 moving the valve 7 away from the sealing face 6. This movement creates a free path or conduit 13 for the fluid to pass to the perforate membrane 5. If the separation of the dose chamber and flexible member 4 is increased after release of the dose and once the dose covers the perforate membrane then this has the potential to apply negative pressure (as described above) to the dose prior to delivery and this can be beneficial for control of fluid meniscus. The interior shape of the dose chamber may have a horizontal surface such as 11 or be shaped conically 12 to help both fluid flow and minimise deposition of suspension particulates. Both are shown in figure, although in practice only one configuration is likely to be employed on a given container.

In FIGS. 1 and 2, the dose is stored in chamber 8 prior to actuation of the device. After actuation, the dose passes into a dose receiving chamber 14 located between the membrane 5, a lower part of chamber 8 and the flexible wall portion 4. Optionally the dose receiving chamber 14 could be wholly or partially filled by a foam material 15 (see FIG. 2) or similar, such as basotect or wicking material, which remains dry during storage, but is capable of retaining the released dose and transmitting the fluid to the perforate membrane through capillary action. This will typically require that at least part of the material 15 remains in contact with the membrane 5 at all times. The material 15 may be in a compressed state when the device is in the configuration of FIG. 1 and may expand when the valve is opened and the device is in the configuration in FIG. 2. This has the advantage of decreasing the orientation dependence of the fluid feed and allowing operation over a greater range of angles. The application of a capillary material in this way can be applied to the different implementations shown in FIGS. 1 to 8.

Figure 3:
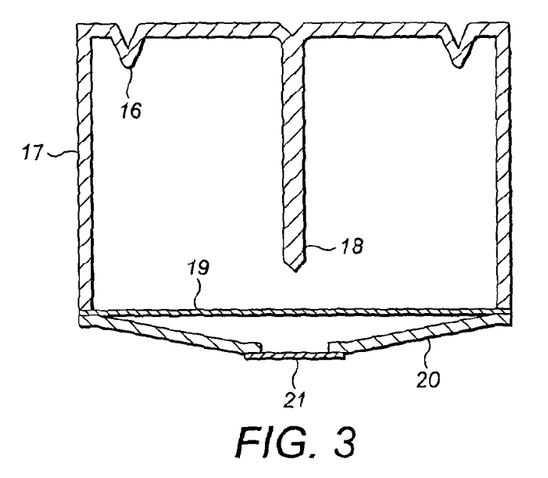
FIG. 3 shows a further example using a different arrangement of the flexible wall.

FIG. 3 shows a form of dose container where the metered dose is retained in the dose container 17 and is sealed in place by a frangible membrane 19, such as a heat sealed foil. A perforate membrane 21 is attached to a conical section 20 and bonded over the frangible membrane so that the liquid dose is separated from the perforate membrane. The dose will be released by pressing the upper surface of the dose container, which is configured to be sufficiently flexible by way of the flexible wall portion 16 (in this case taking the form of a corrugation or the like) to allow the central spike 18 to pierce the frangible membrane. The central spike 18 may be configured to have one or more longitudinal concave sections which on piercing the frangible membrane will form one or more gaps between the spike and the membrane such that liquid and/or air can pass through the gaps. This will facilitate liquid and air exchange once the frangible membrane is pierced.

Figure 4:
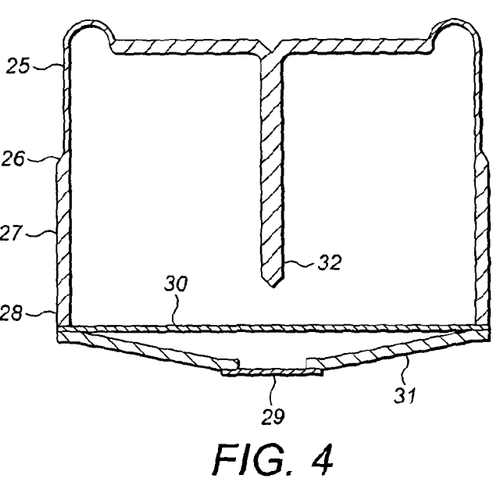
FIGS. 4 and 5 show another example using a different arrangement of the flexible wall in the closed and open positions respectively.

FIG. 4 shows an alternative form for FIG. 3 where the flexibility sufficient to allow piercing of the frangible membrane 30 is incorporated in a roll sock arrangement 35 moulded into the dose chamber 27. The roll sock function is provided by a thinning of wall section 26 to allow movement of the piercing spike 32. In a similar way to FIG. 3 the dose chamber would be moulded as a single piece prior being filled and sealed with a frangible membrane 30 to the edge of dose container 28 and the perforate membrane and conical dose receiving funnel 29 and 30 being sealed to the edge of the frangible membrane.

Figure 5:
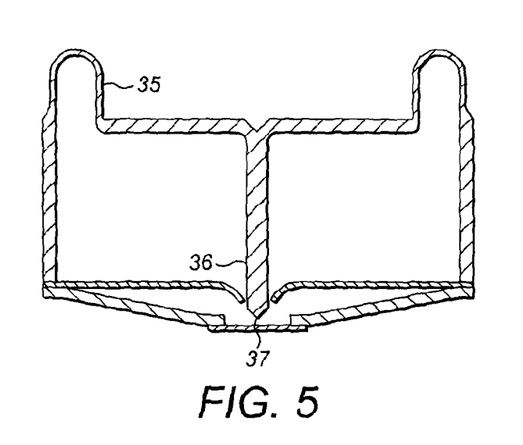

FIG. 5 shows the dose chamber from FIG. 4 once the frangible membrane has been pierced by movement of the spike 36 through movement allowed by the roll sock 35. This movement and piercing of the frangible membrane 30 forms a path or conduit 37 for the fluid to flow to the perforate membrane 29. The cross section of the spike 32 may beneficially be concave to ensure maintenance of the fluid path on piercing the perforate membrane 29.

Figure 6:
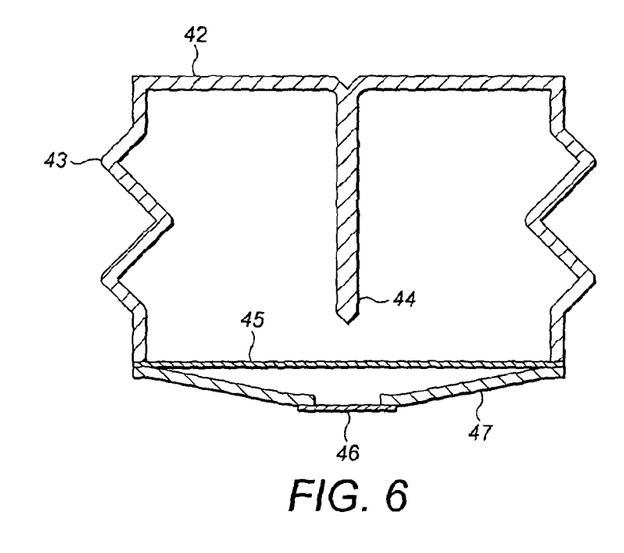
FIG. 6 shows a further example using a different arrangement of the flexible wall using a concertina arrangement.

FIG. 6 shows a third implementation of the piercing style concept where the flexibility to allow piercing of the frangible membrane 47 by spike 44 is provided by a concertina effect 43 moulded as part of the dose chamber 42. Again a perforate membrane 46 and conical dose receiving chamber are sealed to the frangible membrane once the frangible membrane has been applied to the dose.

Figure 7:
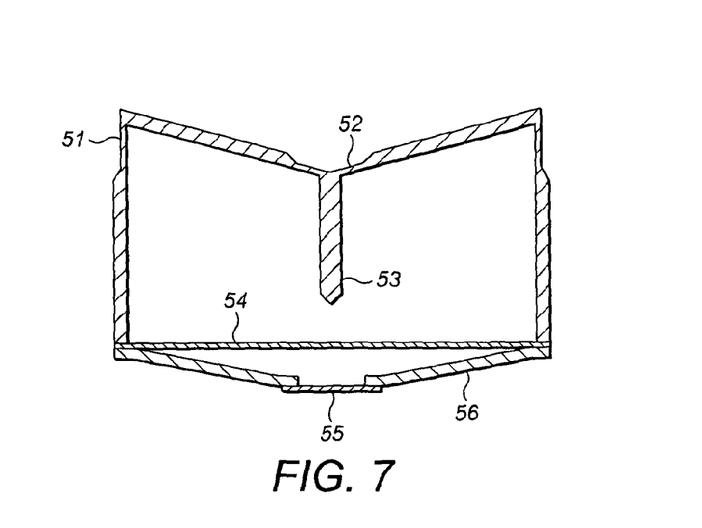
FIGS. 7 and 8 show a further example using a further arrangement of the flexible wall in the closed and open positions respectively.

FIG. 7 shows a third implementation of the piercing concept whereby the piercing action is initiated by a radial rather than an axial compressive force. This is made possible by the thinned wall sections 51 and 52 which allow the shallow conical top to deform to allow internal movement of the piercing spike 53 to pierce the frangible membrane 54. The conical dose receiving cup 56 and perforate membrane 55 are sealed to the edge of the frangible membrane at 57.

FIG. 8 shows the radial action piercing approach after actuation. This shows the edges 62 of the dose chamber pressed in radially such that the central spike 53 has pierced the frangible membrane at point 60.

FIG. 9 illustrates how a number of stacks 67, 68 and 69 of unit doses can be stored within a device. The use of multiple stacks allows space efficient packing of doses. In this form the current dose (9 will be in the delivery position, either connected to a separable actuator (such as a magnetically coupled actuator) or each dose container could incorporate its own actuator. Once the current dose 69 is used then the dose container (including an actuator in the case of a bonded actuator design) will be moved into the adjacent storage stack, position 70 at the point in time when the next dose is needed. In this way doses are presented at the time of use. This transfer to the waste stack 71 will continue for subsequent doses until this stack is full. When dose stack 71 is full then the carousel 66 will rotate such that dose stack 68 becomes the "in use stack and stack 71 becomes the new waste stack. Waste and next doses are advanced in the stack by spring 72 or another similar mechanism.

Figure 10:
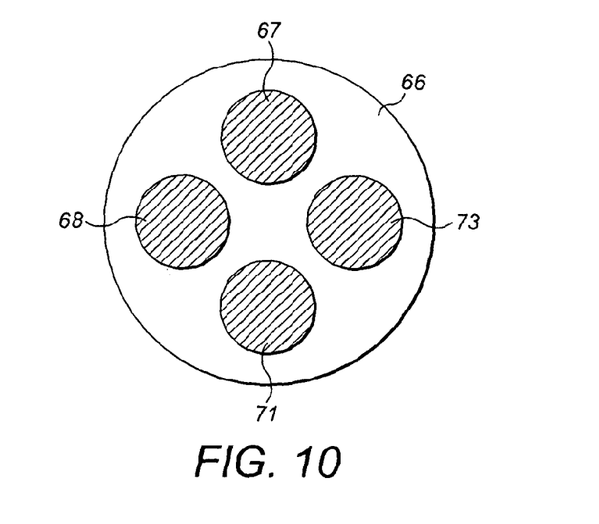
FIG. 10 is an end view of FIG. 9.

FIG. 10 shows the stacks and carousel end on to aid visualisation of the sequence of use of the stacks described in the description of FIG. 9 above. Dose stack 68 is the in use stack with used doses containers moved to stack 71 until stack 68 is empty and 71 is full. The carousel 66 is then rotated so stack 67 is moved to the in use position and stack 68 becomes the new waste stack. This process can be repeated until all three 68, 67 and 73 of the dose stacks are used.

Figure 11:
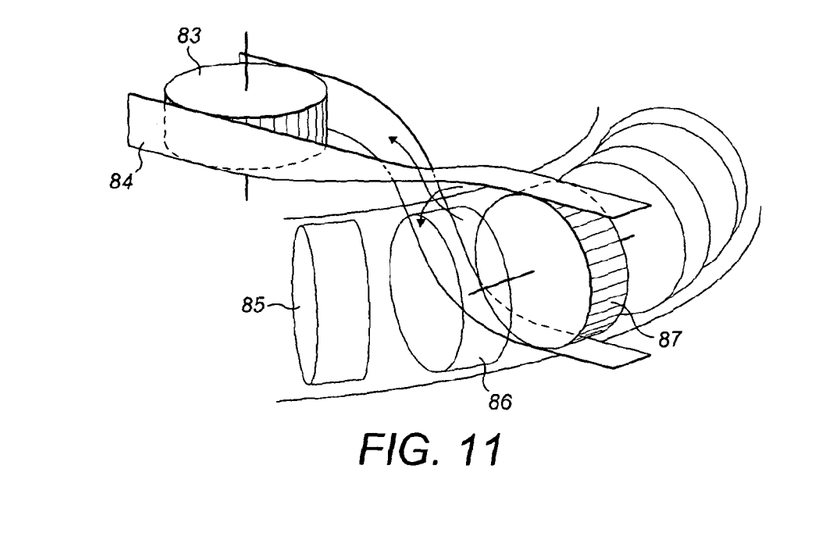
FIG. 11 shows a radially delivery mechanism.

FIG. 11 illustrates an alternative arrangement for storing multiple dose units e.g. 85, 86 and 87 in a compact way. The transfer mechanism in this case moves unit doses to the dispense mechanism along a guide track 84 which includes a significant rotation of orientation, such as 90 degrees of rotation or similar convenient value to orient the unit dose for convenient operation, shown as position 83. The use of the rotation allows the unit doses to be stored in a space efficient way that is compatible with a convenient form factor. If the doses are shaped like truncated segments of a circle then the doses can provide seals for the neighbouring doses.

Figure 12:
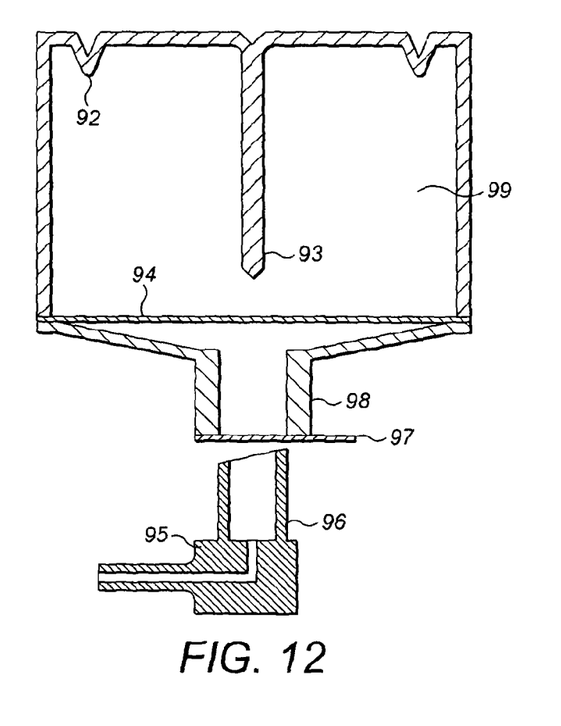
FIGS. 12 and 13 show an example using a jet nebuliser.
Figure 13:
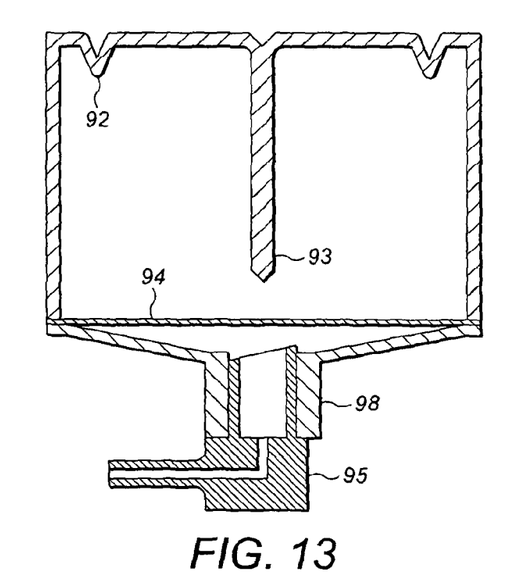
Figure 14:
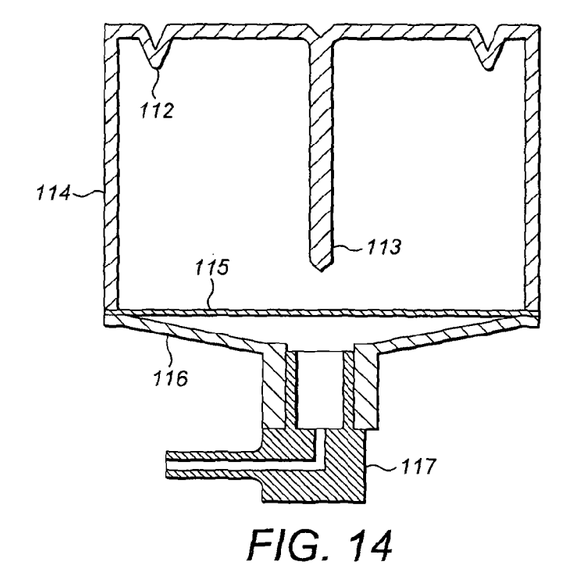
FIG. 14 is a further example using a jet nebuliser.
Figure 15:
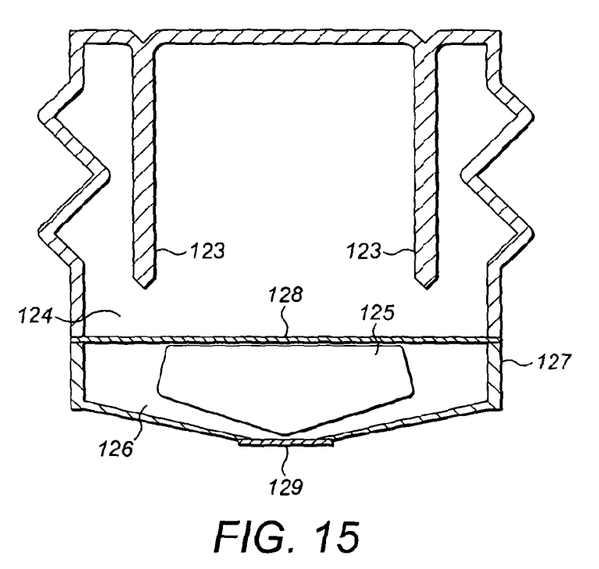
FIGS. 15 and 16 show the provision of a capillary plate in a dose receiving chamber.
Figure 16:
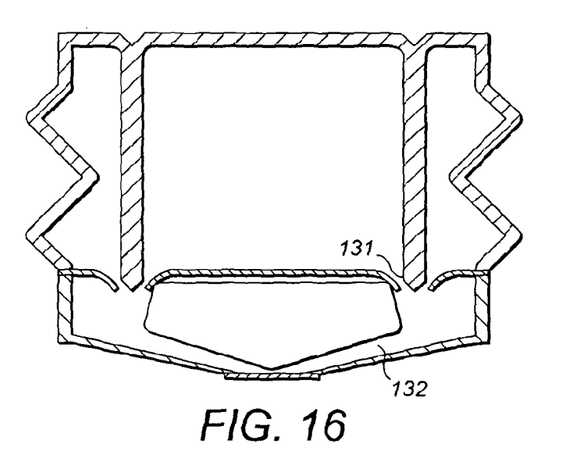

FIG. 12 illustrates an adaptation of a unit dose as described above for FIG. 3, with dose chamber 99, piercing spike 93, flexible element 92, liquid retaining frangible membrane 94 adapted such that elements 98 and 96 can form a fluid seal to a delivery mechanism such as that shown as 95 where the delivery mechanism could be part of a jet nebuliser. This is arranged such that the fluid circuit can be completed before the dose is released and so minimise the chance of spillage and contamination. Optionally a frangible membrane 97 can be used to further protect against contamination until engaged with element 95.

FIG. 13 shows the device described as FIG. 12 with the delivery mechanism engaged ready for receipt of fluid from the dose chamber. The fluid will be released by piercing of the frangible membrane 94 by spike 93 enabled to move by the flexibility of corrugations 92. As with the illustrations above, the internal volume of the dose chamber can be adjusted to control the pressure of the fluid, for example pressurising to prime the device, and neutral of slightly negative to control the location of the fluid meniscus.

FIG. 14 shows a version of the dose chamber where the delivery mechanism 117 is integrated into the dose unit by connection to the fluid receiving cup 116 as such is used once only to maintain sterility. Again the fluid is retained in the dose chamber 114 until the point of use when the frangible membrane 115 is pierced by the spike 113 through the flexibility of the corrugations 112.

In FIGS. 15 and 16, in a similar way to FIGS. 4, 5, 6, 7 and 8, the dose is stored in chamber 124 prior to actuation of the device. After actuation, the dose passes into a dose receiving chamber 126 located between the membrane 128, a lower part of chamber 127 and the perforate membrane 129. Optionally the dose receiving chamber 127 could be partially filled by a capilliary plate 125 or similar, such that the fluid path from the dose chamber 124 to the perforate membrane is formed of a channel or channels of ideally reducing cross section such that fluid is drawn and held in contact with the perforate membrane by capillary forces. Capillary plate 125 should be retained in position such that it is close to, but not touching, the perforate membrane 129. Such a channel is capable of retaining the released dose and transmitting the fluid to the perforate membrane through capillary action. Similarly to the use of foam or wicking material in the dose receiving chamber (FIGS. 1 and 2), this has the advantage of decreasing the orientation dependence of the fluid feed and allowing operation over a greater range of angles. The application of a capillary plate in this way can be applied to the different implementations shown in FIGS. 1 to 8.

When the frangible membrane 128 is pierced by spikes 123, the ensuing fluid path should preferably include both a conduit for liquid towards the perforate membrane and a duct for air to be displaced through. This can be arranged by two spikes 123 as shown or an arrangement of piercing members that generate a fluid path sufficiently large to allow liquid to flow in one direction and air in the other.

The invention claimed is:

1. A unit dose container for holding a single dose of a given liquid, the container comprising:

a chamber in which, in use, the given liquid is stored, the chamber having a wall through which, in use, the liquid is to be supplied to an ambient space;

a release mechanism, at least part of which is internal to, or forms part of the wall of, the chamber, the release mechanism being movable relative to the chamber between first and second positions, the wall of the chamber including at least one flexible wall portion for allowing the release mechanism to move from the first to the second positions, thereby opening a passage through the wall so that the liquid can exit the chamber via the passage in the wall; and a perforate membrane for aerosolising the single dose of the liquid as the liquid exits the chamber into the ambient space via the passage through the wall.

2. A unit dose metering container according to claim 1, wherein the release mechanism includes an internal valve.

3. A unit dose metering container according to claim 1, wherein the release mechanism includes a piercing element for puncturing a frangible membrane to form the passage, the frangible member forming at least a portion of the wall of the chamber within which, in use, the given liquid is stored.

4. A unit dose metering container according to claim 1, wherein the release mechanism is arranged to be operated by an action external to the container.

5. A unit dose metering container according to claim 1, wherein the flexible wall portion is also resilient.

6. A unit dose metering container according to claim 1, comprising means for generating a negative pressure inside the chamber either before or after the dose has been released.

7. A unit dose metering container according to claim 1, wherein the container is configured such that a negative pressure can be created in the chamber during operation.

8. A unit dose metering container according to claim 7, wherein the release mechanism is movable to a third position so as to generate the negative pressure.

9. A unit dose metering container according to claim 1, including means for generating a positive pressure in the chamber.

10. A unit dose metering container according to claim 1, wherein, after the liquid has left the chamber, the release mechanism is configured to return to a position in which the pressure in the chamber returns to ambient pressure.

11. A unit dose metering container according to claim 1, further including connection means to allow connection to a tubular conduit using a radial seal for transfer of the liquid.

12. A unit dose metering container according to claim 1, further including a dose receiving chamber for receiving a dose once the release mechanism has been activated.

13. A unit dose metering container according to claim 12, wherein the dose receiving chamber is filled or partially filled with a capillary material such that the released liquid dose is fed to the point of use by the capillary material thereby increasing the tolerable range of orientation.

14. A unit dose metering container according to claim 13, wherein the capillary material is a foam or wicking material.

15. A unit dose metering container according to claim 1, wherein the dose receiving chamber is at least partially filled by a capillary plate such that the released liquid dose is fed to the point of use by the capillary action thereby increasing the tolerable range of orientation.

16. A multi-pack arrangement of unit dose metering containers according to claim 1, comprising
a carousel having a plurality of radially arranged receiving means for, in use, holding stacks of unit dose metering containers.

17. A multi-pack arrangement according to claim 16, wherein, in use, one of the receiving means is arranged to perform at least one of receiving and storing empty containers following the dispensing of the liquid therein.

18. A unit dose metering container according to claim 1, wherein the perforate membrane is separated from the given liquid in the chamber, during storage of the given liquid, by at least one of an intervening space, a portion of the wall through which the passage extends during supply of the liquid, and a portion of the wall extending substantially perpendicular to movement of the release mechanism between the first and second positions.

* * * * *